US010234936B2

United States Patent
Tanaka et al.

(10) Patent No.: US 10,234,936 B2
(45) Date of Patent: Mar. 19, 2019

(54) SMART WEARABLE DEVICES AND METHODS WITH ATTENTION LEVEL AND WORKLOAD SENSING

(71) Applicants: SONY CORPORATION, Tokyo (JP); SONY CORPORATION OF AMERICA, New York, NY (US)

(72) Inventors: Nobuo Tanaka, Glen Rock, NJ (US); Vladimir Elgort, Staten Island, NY (US); Jacelyn Danielson, San Mateo, CA (US); Anton Kalachev, Burlingame, CA (US); John Wong, Morristown, NJ (US); Behram DaCosta, San Jose, CA (US); Udupi Ramanath Bhat, Mountain View, CA (US); Ludovic Copere, San Jose, CA (US); Masaki Kataoka, Port Washington, NY (US)

(73) Assignees: SONY CORPORATION, Tokyo (JP); SONY CORPORATION OF AMERICA, New York, NY (US)

( * ) Notice: Subject to any disclaimer, the term of this patent is extended or adjusted under 35 U.S.C. 154(b) by 0 days.

(21) Appl. No.: 15/236,450

(22) Filed: Aug. 14, 2016

(65) Prior Publication Data

US 2017/0010667 A1 Jan. 12, 2017

Related U.S. Application Data

(63) Continuation of application No. PCT/US2015/016593, filed on Feb. 19, 2015.
(Continued)

(51) Int. Cl.
*G06F 3/01* (2006.01)
*G06F 1/16* (2006.01)
(Continued)

(52) U.S. Cl.
CPC .............. *G06F 3/011* (2013.01); *G06F 1/163* (2013.01); *G06F 1/1637* (2013.01);
(Continued)

(58) Field of Classification Search
CPC ............. G06F 19/3406; G06F 19/3418; G06F 1/1626; G06F 1/163; G06F 1/1637;
(Continued)

(56) References Cited

U.S. PATENT DOCUMENTS 6,932,359 B2 8/2005 Tamada
8,475,367 B1 7/2013 Yuen et al.
(Continued)

FOREIGN PATENT DOCUMENTS

CN 1860486 A 11/2006
CN 102740933 A 10/2012
(Continued)

OTHER PUBLICATIONS

United States Patent and Trademark Office (USPTO), International Search Report and Written Opinion, PCT International Application No. PCT/US2015/016593, dated Sep. 29, 2015, pp. 1-7, with claims searched, pp. 8-12.
(Continued)

*Primary Examiner* — Tony O Davis
(74) *Attorney, Agent, or Firm* — O'Banion & Ritchey LLP; John P. O'Banion

(57) ABSTRACT

A wearable sensor device, system and method are provided for monitoring the attention, workload or other physical status of the wearer of the wearable sensor device. At least one biometric index value is formulated for a characteristic status from the processed sensor data of the sensors of the device and the biometric index value may also incorporate prior test data and questionnaire response information in the calculated value. The system may include any number of
(Continued)

wearable devices that have sensors, a processor and a communications link as well as a remote computer and a non-wearable device with an interface. The status of the wearer of a wearable sensor device can be monitored with the simple display of the biometric index value as well as the data from the individual sensors.

20 Claims, 3 Drawing Sheets

Related U.S. Application Data

(60) Provisional application No. 61/943,837, filed on Feb. 24, 2014.

(51) Int. Cl.
| | |
|---|---|
| G06F 1/3206 | (2019.01) |
| G06F 1/3234 | (2019.01) |
| G06F 1/3287 | (2019.01) |
| G06F 19/00 | (2018.01) |
| H04L 29/06 | (2006.01) |
| H04W 12/06 | (2009.01) |
| G16H 40/63 | (2018.01) |
| G08B 7/00 | (2006.01) |

(52) U.S. Cl.
CPC ............ *G06F 1/1698* (2013.01); *G06F 1/325* (2013.01); *G06F 1/3206* (2013.01); *G06F 1/3287* (2013.01); *G06F 3/015* (2013.01); *G06F 3/016* (2013.01); *G06F 19/00* (2013.01); *G06F 19/3418* (2013.01); *G16H 40/63* (2018.01); *H04L 63/0861* (2013.01); *H04L 63/0869* (2013.01); *H04W 12/06* (2013.01); *G06F 1/1626* (2013.01); *G08B 7/00* (2013.01); *Y02D 10/171* (2018.01)

(58) Field of Classification Search
CPC ...... G06F 1/1698; G06F 1/3206; G06F 1/325; G06F 1/3287; G06F 3/011; G06F 3/015; G06F 3/016; G08B 7/00; H04L 63/0861; H04L 63/0869; H04W 12/06
USPC ........................................................ 345/156
See application file for complete search history.

(56) References Cited

U.S. PATENT DOCUMENTS

| | | | |
|---|---|---|---|
| 8,527,213 B2 | 9/2013 | Kailas et al. | |
| 2009/0005827 A1 | 1/2009 | Weintraub et al. | |
| 2009/0171180 A1 | 7/2009 | Pering et al. | |
| 2010/0033303 A1* | 2/2010 | Dugan ................. | A61B 5/0002 340/5.82 |
| 2011/0087137 A1* | 4/2011 | Hanoun ............... | A61B 5/0205 600/587 |
| 2011/0173308 A1 | 7/2011 | Gutekunst | |
| 2012/0188158 A1* | 7/2012 | Tan ...................... | A61B 5/0488 345/156 |
| 2012/0316455 A1 | 12/2012 | Rahaman et al. | |
| 2014/0039839 A1 | 2/2014 | Yuen et al. | |
| 2014/0052567 A1* | 2/2014 | Bhardwaj .......... | G06Q 30/0631 705/26.7 |
| 2014/0164632 A1* | 6/2014 | Kim ....................... | H04L 67/34 709/227 |
| 2014/0243710 A1* | 8/2014 | Jeong ................... | A61B 5/1116 600/594 |
| 2014/0277649 A1* | 9/2014 | Chong ................. | G06N 99/005 700/94 |
| 2014/0293059 A1* | 10/2014 | Park ....................... | G01S 19/27 348/158 |
| 2015/0199580 A1* | 7/2015 | Perez .................. | G06K 9/00885 382/115 |
| 2015/0278498 A1* | 10/2015 | Hong ..................... | G06F 21/32 340/5.82 |
| 2016/0039424 A1* | 2/2016 | Hong ................... | B60W 40/08 701/2 |
| 2016/0045135 A1* | 2/2016 | Kim ..................... | A61B 5/6843 600/391 |
| 2016/0070348 A1* | 3/2016 | Cowley ................. | G06F 3/016 345/156 |
| 2016/0086457 A1* | 3/2016 | Baron ..................... | G08B 6/00 340/407.1 |
| 2016/0354042 A1* | 12/2016 | Shim ..................... | G06F 21/32 |
| 2016/0374628 A1* | 12/2016 | Levine ................. | A61B 5/7455 128/848 |
| 2016/0375307 A1* | 12/2016 | Durham ................. | A61B 5/112 482/7 |

FOREIGN PATENT DOCUMENTS

| | | | | |
|---|---|---|---|---|
| CN | 103476152 A | 12/2013 | | |
| EP | 3101577 A1 * | 12/2016 | ............ | G06F 21/32 |
| JP | H11-34688 A | 2/1999 | | |
| JP | 2001-258855 A | 9/2001 | | |
| JP | 2008-229248 A | 10/2008 | | |
| JP | 2009-213707 A | 9/2009 | | |
| JP | 2010-179133 A | 8/2010 | | |
| KR | 10-0609155 A | 8/2006 | | |
| WO | 03/015005 A2 | 2/2003 | | |
| WO | 2006/0544542 A1 | 5/2006 | | |
| WO | 2013/158815 A2 | 10/2013 | | |

OTHER PUBLICATIONS

Japanese Patent Office (JPO), Preliminary Notice of Reasons for Refusal dated Aug. 14, 2017, related Japanese application No. 2016-551210, pp. 1-12, English-language translation, pp. 13-24, with claims examined, pp. 25-29.
Japan Patent Office (JPO), Preliminary Notice of Reasons for Refusal dated Aug. 14, 2017, related Japanese application No. 2016-551210, pp. 1-12, English-language translation, pp. 13-24, with claims examined, pp. 25-29.
Korean Intellectual Property Office (KIPO), Notice of Preliminary Rejection dated Sep. 11, 2017, related Korean application No. 10-2016-7021755, pp. 1-8, English-language translation, pp. 9-15, with claims examined, pp. 16-20.
State Intellectual Property Office of the People's Republic of China (SIPO), Notification of the First Office Action dated May 3, 2018, related Chinese patent application No. 201580007376.8, English-language translation pp. 1-8, Chinese-language document pp. 9-20, claims examined (English-language) pp. 21-26.
Japan Patent Office (JPO), Notification of Reason(s) for Refusal (Official Action) dated Jun. 20, 2018, related Japanese patent application No. 2016-551210, Japanese-language document pp. 1-4, English-language translation pp. 5-8, claims examined pp. 9-11.
Japan Patent Office (JPO), official action dated Dec. 19, 2018, related Japanese patent application No. 2016-551210, pp. 1-3, English-language translation, pp. 4-6, claims examined, pp. 7-9.

* cited by examiner

SMART WEARABLE DEVICES AND METHODS WITH ATTENTION LEVEL AND WORKLOAD SENSING

CROSS-REFERENCE TO RELATED APPLICATIONS

This application is a 35 U.S.C. § 111(a) continuation of PCT international application number PCT/US2015/016593 filed on Feb. 19, 2015, incorporated herein by reference in its entirety, which claims priority to, and the benefit of, U.S. provisional patent application Ser. No. 61/943,837 filed on Feb. 24, 2014, incorporated herein by reference in its entirety. Priority is claimed to each of the foregoing applications.

The above-referenced PCT international application was published as PCT International Publication No. WO 2015/127059 A2 on Aug. 27, 2015, which publication is incorporated herein by reference in its entirety.

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Field of the Technology

This technology pertains generally to smart wearable devices and sensor networks and more particularly to a system of non-wearable and wearable sensor and processing devices for biometric valuation such as attention level and workload sensing.

2. Discussion

Many occupations and activities require the attention and concentration of the participants for often long periods of time. Some occupations, such as air traffic controllers, often require intense concentration to account for and direct aircraft traffic safely through sometimes congested airspace. Other occupations, such as long distance semi-truck or bus driving, require the driver to respond to changing circumstances or events over the duration of the trip to operate safely.

Similarly, other activities, such as learning in different settings, require the attention of the students over the lecture period. The ability of a teacher to successfully teach students is normally dependent on the attention level and mental workload of students at the time of the instruction.

Another problem is slow changing circumstances can also lead to a lack of concentration. For example, a health care provider (e.g., pet owner, parent, caretaker of an elderly individual) may have difficulty determining the health status of a person or pet that needs to be monitored.

However, there are limits to the duration of the ability of humans to concentrate and fatigue, changing physiological conditions, insufficient sleep and boredom can greatly diminish the ability of a person to learn or to operate machinery safely.

There is a need for an apparatus or method for monitoring the attention level and mental workload of individuals in a wide variety of settings. Safety, successful learning, health care and other activities that need persistent attention over time can be improved with constant unobtrusive monitoring.

BRIEF SUMMARY

This disclosure describes smart wearable devices and methods for providing real time monitoring of attention level/mental workload of individuals or groups of individuals through wearable devices. Data from the sensors of each wearable device can be processed and displayed on a remote display or recorded on a remote computer.

Wearable devices have multiple sensors with the capability of collecting biological or physical data (e.g. heart rate, blood oxygen and sugar levels, body temperature etc.) of an individual. Both non-invasive and invasive sensors, alone or collectively, can produce data that can be processed to determine the physical or mental status of the user at a particular instant or demonstrate trends over time.

Other sensors in the wearable device can collect data of the environment surrounding the device including location, altitude, air pollution, pollen count, distance traveled, external temperature etc. that can be considered within the context of the sensor data obtained from a particular user of sensors of a wearable device.

Sensor data processing from each wearable device can be augmented with outside information pertinent to the wearer such as individual health records and outside test results. Questionnaire information can also be incorporated in the attention level/mental workload evaluation.

In one embodiment, a numerical index of attention level or mental workload is generated that accounts for all of the input variables. The index number is a quick value indicator of the status of the individual that can be displayed on the monitor.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

Figure 1:
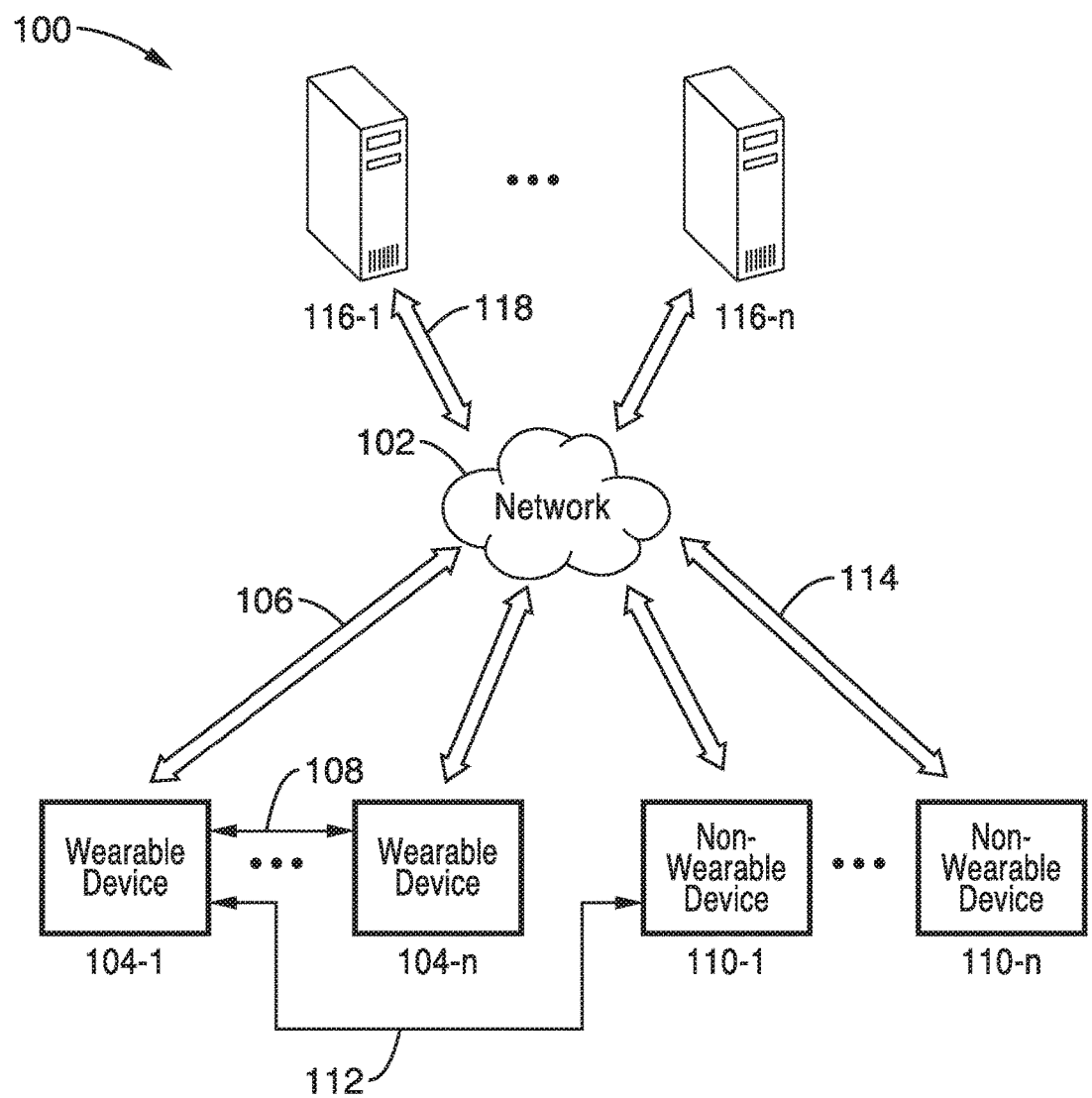
FIG. 1 is a schematic diagram of an embodiment of a smart wearable network described herein.

Referring more specifically to the drawings, for illustrative purposes an embodiment of a wearable apparatus and method for monitoring attention and workload levels based on the processed sensor information and user instruction is described and depicted generally in FIG. 1 through FIG. 4. It will be appreciated that the methods may vary as to the specific steps and sequence and the apparatus may vary as to the elements and structure without departing from the basic concepts as disclosed herein. The method steps are merely exemplary of the order in which these steps may occur. The steps may occur in any order that is desired, such that it still performs the goals of the claimed technology.

The present disclosure generally pertains to wearable devices that are capable of, for example, performing an action based on one or more biological or physiological characteristics of the user wearing the device. Using one or more sensors, a processor, and code executable on the processor, a wearable device can be configured to sense and process characteristics that include, but are not limited to, a wearer's physical characteristics such as gender, weight, height, body temperature, skin temperature, heart rate, respiration, blood sugar level, blood glucose level, stress/fatigue, galvanic skin response, ingestion (protein), digestion rate, metabolic rate, blood chemistry, sweat, core and skin temperature, vital signs, eye dryness, tooth decay, gum disease, energy storage, calorie burn rate, mental alertness, cardiac rhythm, sleep patterns, caffeine content, vitamin content, hydration, blood oxygen saturation, blood coritsol level, blood pressure, cholesterol, lactic acid level, body fat, protein level, hormone level, muscle mass, pH, etc. Such conditions may also include, but are not limited to, position (e.g., prone, upright), movement, or physical state (e.g., sleeping, exercising), etc.

A wearable device may include one or more output devices that include, but are not limited to, haptic output devices (e.g., offset motors, electroactive polymers, capacitive voltage generators, Peltier temperature elements, contracting materials, Braille coding actuators), telemetry devices, visual devices, audible devices, and other output devices.

A wearable device may include an artificial intelligence so that the device can learn and adapt to the wearer. The device may be configured to accurately discriminate between erroneous (accidental, unintended, etc.) and valid sensory inputs, thereby developing accurate conclusions about a wearer's physical state or characteristics (e.g., the device does not interpret a wearer rolling over in their sleep as the wearer exercising). The device may also include one or more cameras or other visual sensors for facial, user, or other image recognition. A wearable device may also be configured to transmit information to and/or retrieve information from a wearer's digital health history.

A wearable device may be configured to output information to a user, to another wearable device, to a non-wearable device, or to a network according to the particular features and function of the device.

A. Generalized System Implementation.

FIG. 1 illustrates a generalized networked infrastructure (e.g., system) 100 that includes a network 102. The network could, for example, be a local area network or a wide area network such as the Internet. One or more smart wearable devices 104-1 through 104-n according to embodiments of the technology described herein may be enabled to communicate with the network 102 through a wired or wireless connection 106. Further, one or more of the smart wearable devices may be enabled to communicate with another smart wearable device through the network 102 or by means of a direct wired or wireless connection 108.

One or more of the smart wearable devices 104-1 through 104-n also may be enabled to communicate with one or more non-wearable devices 110-1 through 110-n. The non-wearable devices, which are beyond the scope of this disclosure, may be any conventional "smart" device with a processor, associated operating system, and communications interface. Examples of non-wearable devices include smart phones, tablet computers, laptop computers, desktop computers, and set top boxes. Any of the non-wearable devices may be of a type enabled to communicate with an external device through a wired or wireless connection. In that case, one or more of the smart wearable devices may be enabled to communicate with one or more of the non-wearable devices by means of a direct wired or wireless connection 112. Further, one or more of the non-wearable devices may be of a type enabled to communicate with the network 102 through a standard wired or wireless connection 114. In that case, one or more of the smart wearable devices may be enabled to communicate with one or more of the non-wearable devices through the network 102.

One or more servers 116-1 through 116-n may be provided in a client-server configuration and connected to the network by means of a wired or wireless connection 118. The servers may include standalone servers, cluster servers, networked servers, or servers connected in an array to function like a large computer. In that case, one or more of the smart wearable devices may be enabled to communicate with one or more of the servers.

Figure 2:
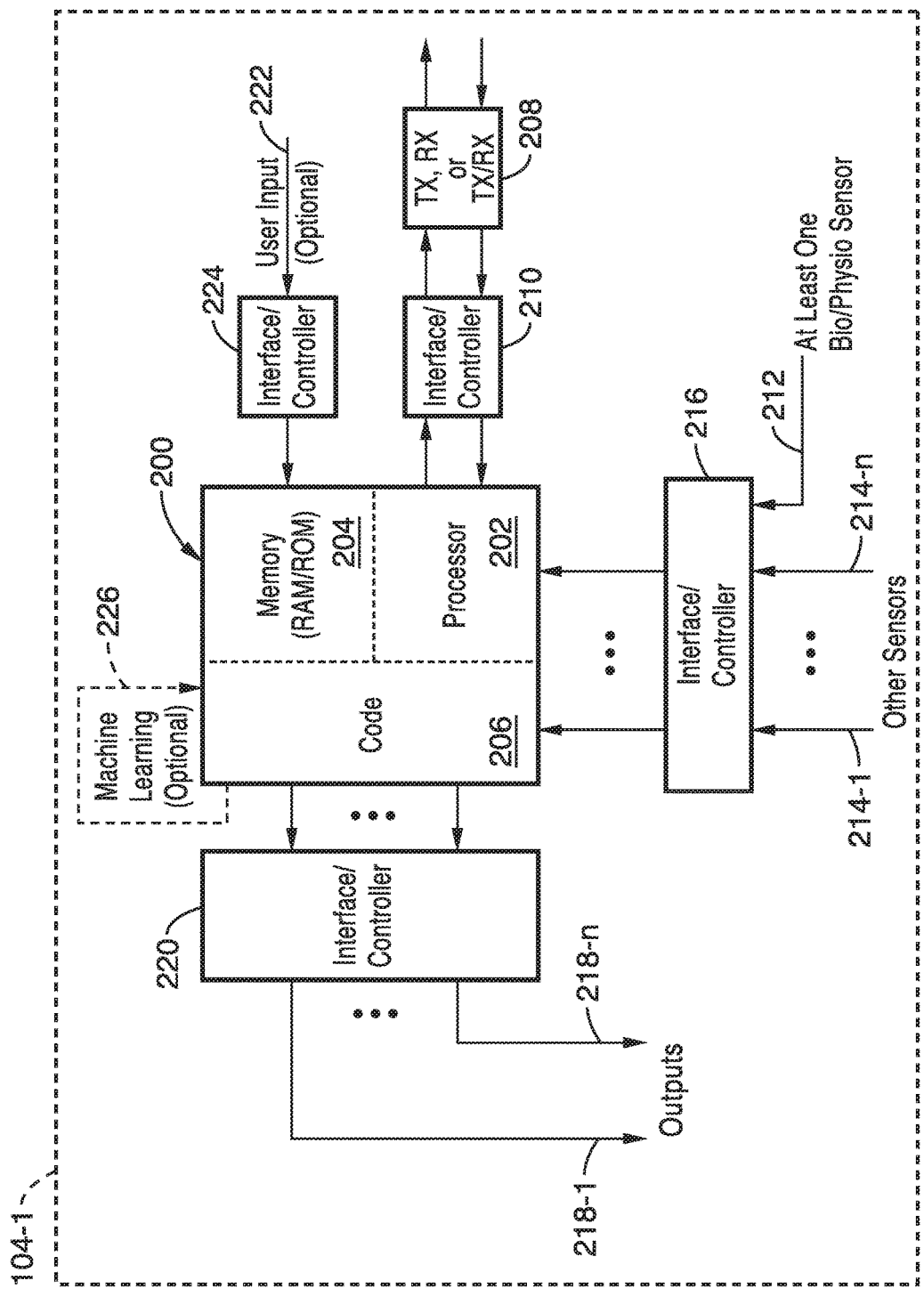
FIG. 2 is a functional block diagram of an embodiment of a smart wearable device described herein.

FIG. 2 illustrates a generalized embodiment of a smart wearable device according to the technology described herein. It will be appreciated that the embodiment shown may be modified or customized to enable performing the functions described herein. In the exemplary embodiment shown, the smart wearable device includes an "engine" 200 having a processor 202, memory 204, and application software code 206. The processor 202 can be any suitable conventional processor. The memory 204 may include any suitable conventional RAM type memory and/or ROM type memory with associated storage space for storing the application programming code 206.

A conventional wired or wireless communications module 208 (e.g., transmitter or receiver or transceiver) may be included as needed for performing one or more of the functions of the smart wearable device described herein. Examples of wireless communication capabilities that can be provided including, but are not limited to, Bluetooth, Wi-Fi, infrared, cellular, and near field communication. One or more conventional interfaces or controllers 210 may also be provided if needed. Examples of interfaces or controllers include, but are not limited to, analog to digital converters, digital to analog converters, buffers, etc.

The device may include at least one input 212 for a biological or physiological sensor for providing input to the device to perform one or more of the functions described herein. Sensor inputs 214-1 through 214-n for optional sensors may be included as well. These optional input sensors may include, but are not limited to, accelerometers, temperature sensors, altitude sensors, motion sensors, position sensors, and other sensors to perform the function(s) described herein. One or more conventional interfaces or controllers 216 may be provided if needed for the sensors. Examples of interfaces or controllers include, but are not limited to, analog to digital converters, digital to analog converters, buffers, etc.

Additionally, the device may include one or more outputs 218-1 through 218-n to drive one or more output devices. These output devices may include, but are not limited to, haptic output devices, telemetry devices, visual devices, audible devices, and other output devices to perform the functions described herein. One or more conventional interfaces or controllers 220 may be provided if needed for the output devices. Examples of interfaces or controllers include, but are not limited to, analog to digital converters, digital to analog converters, buffers, etc.

A user input 222 may be provided according to the functions described herein. The user input may, for example, initiate one or more functions, terminate one or more functions, or intervene in a running process. The user input can be any conventional input device, including but not limited to, manual switches, touch sensors, magnetic sensors, proximity sensors, etc. One or more conventional interfaces or controllers 224 may be provided if needed for the output devices. Examples of interfaces or controllers include, but are not limited to, analog to digital converters, digital to analog converters, buffers, etc.

Depending on the function(s) described herein, the engine 200 may also include a feedback loop 226 for machine learning or other adaptive functions. The feedback loop may also provide for device calibration.

It will be appreciated that a smart wearable device as described herein would necessarily include a housing or carrier for the above-described components. It will further be appreciated that, as used herein, the term "smart wearable device" means a device that would be worn or otherwise associated with the body of a user and be "connected" to the user by means of at least one sensor for sensing one or more biological or physiological conditions of the user.

The particular form of the housing or carrier (i.e., wearable platform) can vary according to choice and suitability for performing the functions described herein. Examples of wearable platforms include, but are not limited to, hand worn devices, finger worn devices, wrist worn devices, head worn devices, arm worn devices, leg worn devices, ankle worn devices, foot worn devices, toe worn devices, watches, eyeglasses, rings, bracelets, necklaces, articles of jewelry, articles of clothing, shoes, hats, contact lenses, gloves, etc.

It will further be appreciated that the input sensors and output devices may be integrated into the wearable platform, or may be external to the wearable platform, as is desired and/or suitable for the function(s) of the smart wearable device.

B. Smart Wearable Device for Monitoring Attention Levels.

Figure 3:
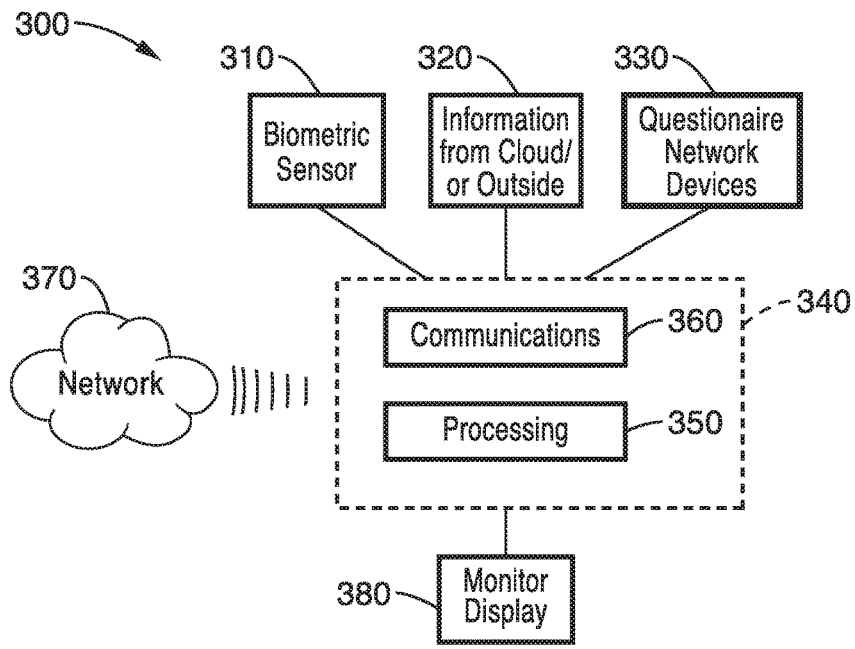
FIG. 3 is a schematic functional diagram of one embodiment of a wearable device system described herein.

Turning now to FIG. 3, a configuration of a wearable device and remote display and remote computer of one embodiment is schematically shown. The wearable device system 300 is described in the context of monitoring an individual wearer. For example, a long distance truck driver could be monitored remotely through a wearable device.

However, it will be understood that multiple wearers can also be monitored with the system from a single display. For example, the ability of a teacher to teach a classroom of students may be improved by determining the attention level/mental workload of students through wearable devices worn by the students in a classroom. The teacher could view the attention level status of each student as well as average attention levels for the class.

In the embodiment shown in FIG. 3, a wearable device 340 is worn by a selected individual to be monitored. The wearable device includes one or more a biological or physiological sensors 310 for acquiring biological input about the user. This sensor data input may be acquired through automatically sensing and collecting biological information about the wearer. The data from biometric sensors and environmental sensors may be also be supplemented with outside information 320 about the wearer such as health conditions as well a past health questionnaires or contemporaneous user input 330.

In one embodiment, a networked device such as a tablet or smart phone is used to provide status of the wearer through responses to questions in a status inquiry form at block 330. The replies can be transmitted or sent electronically to the wearable device for processing. The replies to the status inquiry form and outside information 320 can be used in combination with the sensor data 310 to determine current attention and workload levels.

The wearable device 340 shown in FIG. 3 has a processing module 350 with programming, computation, memory and storage elements. The device also has a communications link 360 that can transmit and receive communications wirelessly to communicate with remote computing, interface and display devices such as a remote computer server 370 or a non-wearable device.

The display 380 can be a linked wirelessly with a network or directly with the wearable device typically through the communications link 360. The display 380 can be a conventional computer monitor or it can be a display of a tablet or smart phone etc.

In one embodiment, the processing of sensor data takes place on a remote computer 370 from a stream of sensor data transmitted to the computer. Instructions and results are then transmitted back for display on the display 380. In another embodiment, the display 380 is part of the remote computer 370. For example, the wireless devices of students in a class are networked with the computer of the teacher that processes the data and displays attention and workload status of each student.

The wearable device 340 may be programmed to determine a physical and mental status of the user, and when a given status is determined, the smart warble device may automatically generate an index number, colored symbol or grade or other indicator of attention level or workload level that can be sent to the display 380 or to other devices such as a remote computer 370.

For example, the attention and workload levels of a long distance semi-truck driver could be monitored by the company to improve the safety of the driver and of the public. The wearable device of the driver could regularly transmit computed status indicators to the trucking company. The company can alert the driver or direct the driver to stop if the status indicator goes beyond a level that is considered to be safe for that driver. The company can also verify that the driver had an appropriate sleep period because the wearable device can determine if the driver is asleep.

Figure 4:
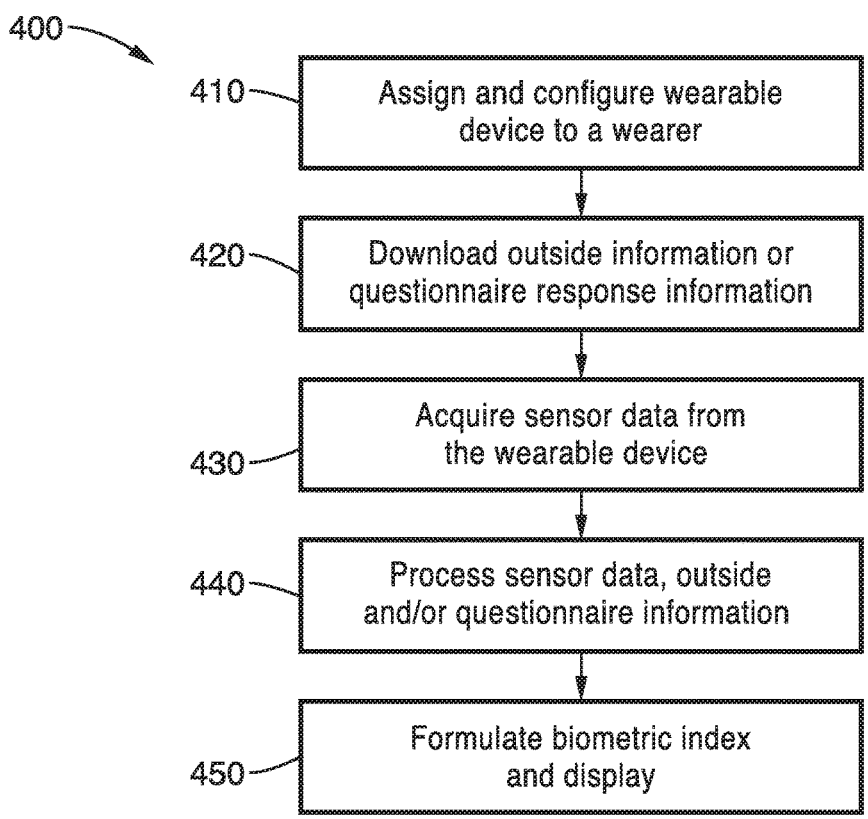
FIG. 4 is a schematic flow diagram of one embodiment of the method for biometric monitoring such as attention/workload monitoring.

One method 400 for monitoring the attention level and workload level of a wearer of a wearable device is shown in FIG. 4. At block 410 of FIG. 4, the wearable device is assigned to a specific wearer and may be configured with sensors for a particular or a general purpose. The sensors that are selected for the wearable device should include one or more biometric sensors relating to attention level or workload. In one embodiment, the wearable device has many different sensors but only a select few are actuated when the device is assigned to a specific user at block 410 and is tailored for a particular condition to be monitored.

Optionally, outside information and questionnaire information is collected and stored on the wearable device or at a remote computer where sensor data processing will take place at block 420. The outside information obtained at block 420 may include a defined set of ranges or health conditions or limitations that may be relevant to the evaluation of the present physical status of the wearer. The outside information may include invasive test results such as blood test results. Questionnaire responses may also be included at block 420. Questionnaire inquiries may be specific to the conditions being monitored with the wearable device. For example, sleep duration, time of the last meal or snack, allergy information and other related information that is helpful in determining status can be obtained through the questionnaire.

The sensor data is acquired from the sensors of the wearable device at block 430. The sensor data can be acquired continuously or periodically at block 430. The acquired sensor data can be collected and stored within the device or it can be sent to a remote computer for remote storage and processing.

For example, wearable devices may be worn by the person or pet in order to determine via one or more sensors e.g., hydration, blood sugar, blood glucose, $SPO_2$ (blood oxygen saturation), cortisol (stress), blood pressure, heart & galvanic skin (stress), cholesterol, lactic acid (muscle fatigue), sleep type, fat % in body, protein %, muscle mass, hormones, body temperature, PH (acidity) in the stomach), variability of heart rate, breathing by-products, endothelial (arteries), or skin health.

The sensor data that is acquired at block 430 is processed at block 440 of FIG. 4 along with any outside information and/or questionnaire information that was obtained at block 420. Sensor data that is collected from the wearable devices can be evaluated for levels that are above or below predefined levels. For example, it can be determined whether the blood sugar of the individual is below a particular level or range of levels or whether hydration is below a certain level. It can be determined whether the individual received enough sleep by calculating the appropriate amount of sleep the night before with the amount identified in response to a questionnaire inquiry. Other evaluations could be whether the individual's body temperature is above one temperature or below another or whether the pupillary response or the oxygen levels are within acceptable ranges. Any number of evaluations can be performed to form conclusions regarding the status of the wearer.

At block 450, a biometric index value is formulated and displayed on the display. The formulated index value may also be recorded either on the wearable sensor device or on the display device or on the remote computer. The formulated index value at block 450 may also be compared to a designated threshold index level. If the formulated index value exceeds or is less than the designated threshold, then a notification can be displayed on the display device or an alarm can be initiated. In one embodiment, the formulated index values and an alarm or warning can be sent to a remote display device such as a smart telephone or tablet of the subject being monitored or to a third party to let them know of the questionable status. The feedback loop of this embodiment can give real time status information and warnings when the index values go beyond desired levels.

The biometric index value is formulated from a composite of information and sensor data values that indicate the present condition of the wearer. The biometric index is preferably a number on a scale that accurately indicates the present condition of the wearer. In another embodiment, the biometric index is a letter such as "A" through "D" where each letter designation corresponds to a possible physical status condition of the wearer of the device. In another embodiment, the biometric index displayed a color such as green, yellow and red and each color represents an alert status for selected physical conditions.

Another adaptation of the system and methods is with an assessment of an overall level of stress. It has been shown that a healthy or stress free person tends to have periodic cycles of rapid eye movement (REM) sleep and non-rapid eye movement (non-REM) sleep. However, the periodic cycles of REM sleep and non-REM sleep are disrupted when a person is under various levels of stress. The wearable device may detect the level of stress by measuring the cycle of REM sleep and non-REM sleep, particularly by measuring the regularity of the period of REM sleep and non-REM sleep. The typical cycle of REM sleep and non-REM sleep begins with non-REM sleep when the person goes into sleep. The period of a set of REM sleep and non-REM sleep tends to be around 90 minutes. In the 90 minutes, REM sleep and non-REM sleep alternates. Therefore, it is preferable that the wearable device sores the information of this typical period of a set of REM sleep and non-REM sleep, for example, in memory 204. Also, the wearable device may use that information to decide whether the user is in REM sleep or non-REM sleep.

In one preferred embodiment, the wearable device is wristband type of wearable device that has an accelerometer, a heart pulse monitor, and a clock that are monitored when the wearer is sleeping. The accelerometer can monitor the movements of the wearer when the subject is sleeping. The software running on the processor 202 together with the peripheral circuit components such as memory 204 analyzes the signal from the accelerometer as well as the other sensors.

The signal from the accelerometer represents the three dimensional movement of the wearable device. The motion signal from the accelerometer will include a characteristic pattern. For example, when the wearer is walking, the signal from an accelerometer has a unique pattern to the motion of the wearer such as a periodically shown pattern in the signal. The processor 202, by using the code 206, can retrieve a unique pattern attributed to a walking motion that is hidden in the signal and identify the type of the motion of the user. By applying this type of methodology, the wearable device can identify the status of the wearer, such as the status that the wearer is sleeping.

REM sleep is a stage of sleep characterized by the rapid and random movement of the eyes where a depth of the sleep is not deep. On the other hand, the non-REM sleep is a stage of sleep where the depth of sleep is considered to be deep. It has also been shown that a person in non-REM sleep tends to turn over with some frequency. The turnover can be identified by the accelerometer.

Another characteristic of non-REM sleep is that the heart pulse is steady and the rhythm of breathing is steady and these characteristics can be monitored. For example, the wearable device may use a heart pulse monitor together with an accelerometer and a clock to identify whether the wearer is in REM sleep or in non-REM sleep. For example, the wearable device may decide that the user is in non-REM sleep when the accelerometer detects more wearer's turnover than other times (i.e., REM sleep) and when the heart pulse monitor detects the steady heart pulse. This may be realized by the instructions as a form of code 206. Using both of the accelerometer and the heart pulse monitor is expected to increase the likelihood of accurately detect a type of sleep of the wearer (e.g., non-REM sleep or REM sleep). In addition, the clock information, alone or in combination of the accelerometer and the heart pulse monitor, can be used to detect whether the wearer is in non-REM sleep or in REM sleep.

Accordingly, the wearable device system programming can automatically sense biological and environmental conditions of the wearer of the device and processes the sensor data and other relevant information and can formulate an index representing the composite of sensor results that can be quickly and easily understood when displayed on a display. The physical condition or conditions of the wearer can be monitored easily by the wearer as well as outside observers. The system allows for the constant monitoring of the attention or workload or other aspect of an individual's health without them continuously being connected to bulky and frequently wired healthcare-related machines.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that "programming" as used herein refers to one or more instructions that can be executed by a processor to perform a function as described herein. The programming can be embodied in software, in firmware, or in a combination of software and firmware. The programming can be stored local to the device in non-transitory media, or can be stored remotely such as on a server, or all or a portion of the programming can be stored locally and remotely. Programming stored remotely can be downloaded (pushed) to the device by user initiation, or automatically based on one or more factors, such as, for example, location, a timing event, detection of an object, detection of a facial expression, detection of location, detection of a change in location, or other factors. It will further be appreciated that as used herein, that the terms processor, central processing unit (CPU), and computer are used synonymously to denote a device capable of executing the programming and communication with input/output interfaces and/or peripheral devices.

From the discussion above it will be appreciated that the technology can be embodied in various ways, including but not limited to the following:

1. A wearable sensor apparatus, comprising: (a) a computer processor with memory; (b) a plurality of sensors operably coupled to the processor; (c) a display; (d) programming in a non-transitory computer readable medium and executable on the computer processor for performing steps comprising: (i) acquiring sensor data from one or more sensors worn by a wearer; (ii) processing the acquired sensor data from each sensor; (iii) formulating at least one biometric index value from the processed sensor data; and (iv) displaying the biometric index value on the display.

2. An apparatus as recited in any previous embodiment, wherein the biometric index value formulation further incorporates prior biological test data of the wearer.

3. An apparatus as recited in any previous embodiment, wherein the biometric index value formulation further incorporates contemporaneous wearer submitted status information.

4. An apparatus as recited in any previous embodiment, wherein the plurality of sensors comprises: at least one biological sensor configured to measure an internal physical condition of a wearer; and at least one non-biological sensor configured to measure an external condition of a wearer.

5. An apparatus as recited in any previous embodiment, the wearable apparatus further comprising: (a) a communications link operably coupled to the processor, the link having a transmitter and receiver; and (b) programming in a non-transitory computer readable medium and executable on the computer processor for performing steps comprising: (i) communicating acquired sensor data to a remote computer; and (ii) executing program commands received from the remote computer.

6. A wearable sensor apparatus monitoring system, comprising: (a) at least one wearable sensor device, comprising: (i) a computer processor with memory; (ii) a plurality of sensors operably coupled to the processor; (iii) a communications link; and (iv) programming in a non-transitory computer readable medium and executable on the computer processor for performing steps comprising: 1. acquiring sensor data from one or more sensors worn by a user; 2. communicating with a monitor and display device through the communications link; and (b) a monitor and display device, comprising: (i) a communications link; (ii) a computer processor with memory; (iii) a display; and (iii) programming in a non-transitory computer readable medium and executable on the computer processor for performing steps comprising: 1. sending and receiving communications from each wearable sensor device; 2. processing sensor data received from each wearable sensor device; 3. formulating at least one biometric index value from the processed sensor data for each wearable sensor device; and 4. displaying the biometric index value on the display.

7. A system as recited in any previous embodiment, wherein the biometric index value formulation further incorporates prior biological test data of the wearer.

8. A system as recited in any previous embodiment, wherein the biometric index value formulation further incorporates contemporaneous wearer submitted status information.

9. A system as recited in any previous embodiment, the system further comprising: a non-wearable device with a communications link, computer processor with memory, display and user interface.

10. A system as recited in any previous embodiment, wherein the non-wearable device of the system further comprises an alarm configured to actuate if at least one biometric index value exceeds a designated range.

11. A system as recited in any previous embodiment, wherein contemporaneous wearer submitted status information is entered through the user interface and communicated to the wearable device or to the display device through the communications link.

12. A system as recited in any previous embodiment, wherein the user interface of the non-wearable device further comprises a programming interface configured to control the sensors and computer processor of the wearable device over the communications link.

13. A computer implemented method for monitoring a wearer of a wearable device, the method comprising: (a) acquiring sensor data from at least one sensor of a wearable device worn by a user; (b) processing the acquired sensor data from each sensor; and (c) formulating at least one biometric index value from the processed sensor data from the sensors of the wearable device; (d) wherein the method is performed by executing programming on at least one computer processor, the programming residing on a non-transitory medium readable by the computer processor.

14. A method as recited in any previous embodiment, further comprising: downloading outside prior biological test data and prior sensor data of the user; and using the prior data with the acquired sensor data in the formulation of the biometric index values.

15. A method as recited in any previous embodiment, further comprising: providing a questionnaire of inquiries pertaining to the current status of the wearer; and using the responses to the questionnaire inquiries with the acquired sensor data in the formulation of the biometric index values.

16. A method as recited in any previous embodiment, further comprising: transferring acquired sensor data from the wearable device to a remote computer; processing the transferred sensor data; formulating biometric index values from the processed data; and displaying the biometric index values for each wearable device on a display.

17. A method as recited in any previous embodiment, further comprising: transmitting biometric index values from the remote computer to a smart telephone when the index values exceed a set threshold value.

18. A method as recited in any previous embodiment, wherein the sensors comprise: at least one biological sensor configured to measure an internal physical condition of a wearer; and at least one non-biological sensor configured to measure an external condition of a wearer.

19. A method as recited in any previous embodiment, wherein the sensors comprise an accelerometer, a heart monitor and a clock; and wherein the formulated biometric index value comprises a level of stress formulated from processed sensor data of a subject during REM and non-REM sleep.

Although the description above contains many details, these should not be construed as limiting the scope of the technology but as merely providing illustrations of some of the presently preferred embodiments of this technology. Therefore, it will be appreciated that the scope of the present technology fully encompasses other embodiments which may become obvious to those skilled in the art, and that the scope of the present technology is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present technology, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112 unless the element is expressly recited using the phrase "means for" or "step for".

What is claimed is:

1. A wearable biometric sensor apparatus, comprising:
   (a) a computer processor with memory;
   (b) a plurality of sensors operably coupled to the processor, wherein said sensors are configured to collect biological and environmental data;
   (c) a display;
   (d) programming in a non-transitory computer readable medium and executable on the computer processor for performing steps comprising:
      (i) acquiring sensor data from said plurality of sensors configured for being worn by a wearer;
      (ii) processing the acquired sensor data from each sensor and evaluating levels that are above or below pre-defined levels;
      (iii) formulating at least one biometric index value from a composite of the processed sensor data to indicate the present condition of the wearer as a number on a scale; and
      (iv) displaying the biometric index value on the display.

2. The apparatus of claim 1, wherein said biometric index value formulation further incorporates prior biological test data of the wearer.

3. The apparatus of claim 1, wherein said biometric index value formulation further incorporates contemporaneous wearer submitted status information.

4. The apparatus of claim 1, wherein said plurality of sensors comprise:
   at least one biological sensor configured to measure an internal physical condition of a wearer; and
   at least one non-biological sensor configured to measure an external condition of a wearer.

5. The apparatus of claim 1, said wearable apparatus further comprising:
   (a) a communications link operably coupled to the processor, the link having a transmitter and receiver; and (b) programming in a non-transitory computer readable medium and executable on the computer processor for performing steps comprising:
  (i) communicating acquired sensor data to a remote computer; and
  (ii) executing program commands received from the remote computer.

6. A wearable biometric sensor apparatus and monitoring system, comprising:
  (a) at least one wearable sensor device, comprising:
    (i) a computer processor with memory;
    (ii) a plurality of sensors operably coupled to the processor, wherein said sensors are configured to collect biological and environmental data;
    (iii) a communications link; and
    (iv) programming in a non-transitory computer readable medium and executable on the computer processor for performing steps comprising:
      1. acquiring sensor data from said plurality of sensors configured for being worn by a wearer;
      2. communicating with a monitor and display device through the communications link; and
  (b) a monitor and display device, comprising:
    (i) a communications link;
    (ii) a computer processor with memory;
    (iii) a display; and
    (iv) programming in a non-transitory computer readable medium and executable on the computer processor for estimating attention level and workload level based on performing steps comprising:
      1. sending and receiving communications from each wearable sensor device;
      2. processing sensor data received from each wearable sensor device and evaluating sensor data levels that are above or below predefined thresholds;
      3. formulating at least one biometric index value for attention level and workload level of the wearer based on processing evaluated sensor data levels that are above or below pre-defined levels to indicate the present condition of the wearer as a number on a scale; and
      4. displaying the biometric index value on the display.

7. The system of claim 6, wherein said biometric index value formulation further incorporates prior biological test data of the wearer.

8. The system of claim 6, wherein said biometric index value formulation further incorporates contemporaneous wearer submitted status information.

9. The system of claim 6, said system further comprising: a non-wearable device with a communications link, computer processor with memory, display and user interface.

10. The system of claim 9, wherein said non-wearable device of said system further comprises an alarm configured to actuate if at least one biometric index value exceeds a designated range.

11. The system of claim 9, wherein contemporaneous wearer submitted status information is entered through the user interface and communicated to the wearable device or to the display device through the communications link.

12. The system of claim 9, wherein said user interface of the non-wearable device further comprises a programming interface configured to control the sensors and computer processor of the wearable device over the communications link.

13. The wearable biometric sensor apparatus of claim 6, wherein said instructions when executed by the computer processor further perform steps comprising comparing said biometric index value with a predetermined threshold value and generating a notification and/or alarm on the display.

14. A computer implemented method for biometric sensing and monitoring a wearer of a wearable device, the method comprising:
  (a) acquiring sensor data from a plurality of sensors, including biological and environmental sensing, of a wearable device worn by a user;
  (b) processing the acquired sensor data from each sensor and evaluating levels that are outside of pre-defined levels; and
  (c) formulating at least one biometric index value from a composite of the processed sensor data to indicate the present condition of the wearer as a number on a scale from the sensors of the wearable device;
  (d) displaying the biometric index value on a display;
  (e) wherein said method is performed by executing programming on at least one computer processor, said programming residing on a non-transitory medium readable by the computer processor.

15. The method of claim 14, further comprising:
downloading outside prior biological test data and prior sensor data of the user; and
using the prior data with the acquired sensor data in the formulation of said biometric index values.

16. The method of claim 14, further comprising:
providing a questionnaire of inquiries pertaining to the current status of the wearer; and
using the responses to the questionnaire inquiries with the acquired sensor data in the formulation of said biometric index values.

17. The method of claim 14, further comprising:
transferring acquired sensor data from the wearable device to a remote computer;
processing the transferred sensor data;
formulating biometric index values from the processed data; and
displaying the biometric index values for each wearable device on a display.

18. The method of claim 17, further comprising:
transmitting biometric index values from the remote computer to a smart telephone when the index values exceed a set threshold value.

19. The method of claim 14, wherein said sensors comprise:
at least one biological sensor configured to measure an internal physical condition of a wearer; and
at least one non-biological sensor configured to measure an external condition of a wearer.

20. The method of claim 14, wherein said sensors comprise an accelerometer, a heart monitor and a clock; and wherein said formulated biometric index value comprises a level of stress formulated from processed sensor data of a subject during REM and non-REM sleep.

* * * * *